United States Patent [19]
Nakao et al.

[11] Patent Number: 5,814,052
[45] Date of Patent: Sep. 29, 1998

[54] SURGICAL CAUTERIZATION SNARE WITH LIGATING SUTURE

[76] Inventors: Naomi L. Nakao, 303 E. 57th St., New York, N.Y. 10022; Peter J. Wilk, 185 W. End Ave., New York, N.Y. 10023

[21] Appl. No.: 496,574

[22] Filed: Jun. 29, 1995

[51] Int. Cl.$^6$ .................................................. A61B 17/24
[52] U.S. Cl. ...................... 606/115; 606/110; 606/113; 606/114
[58] Field of Search .................... 606/110, 111, 606/113, 148, 115, 114

[56] References Cited

U.S. PATENT DOCUMENTS

| | | | |
|---|---|---|---|
| 5,336,227 | 8/1994 | Nakao et al. | 606/110 |
| 5,397,320 | 3/1995 | Essig et al. | 606/110 |
| 5,417,697 | 5/1995 | Wilk et al. | 606/113 |
| 5,423,830 | 6/1995 | Schneebaum et al. | 606/110 |

*Primary Examiner*—Michael Powell Buiz
*Assistant Examiner*—Mark S. Leonardo
*Attorney, Agent, or Firm*—Abelman, Frayne & Schwab

[57] ABSTRACT

A surgical instrument assembly for use in snare cauterization operations includes a first tubular sheath member containing a metallic electrical snare cauterization loop. A second tubular sheath member is disposed inside of the first tubular sheath member. A flexible suture member is releasably connected to the cauterization loop, and is provided with a one-way slip knot at its distal end thereby forming a loop of a size corresponding to that of the cauterization loop. The proximal end of the suture member is disposed in the distal end of the second tubular sheath member and is releasably joined to a manually-controlled flexible tensioning device. During use of the instrument, the cauterization loop and connected suture member is expanded from a collapsed configuration and passed over a polyp or other body tissue that is to be removed. The suture member is released from the cauterization loop, the slip knot is tightened around the base of the polyp or body tissue to effect ligation, the cauterization loop is tightened around the free end of the polyp and severed. The stalk of the polyp remains securely ligated by the suture.

29 Claims, 8 Drawing Sheets

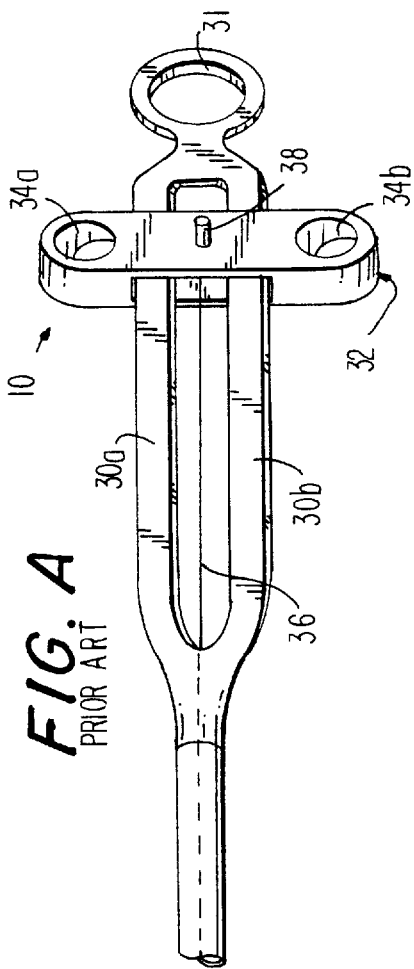
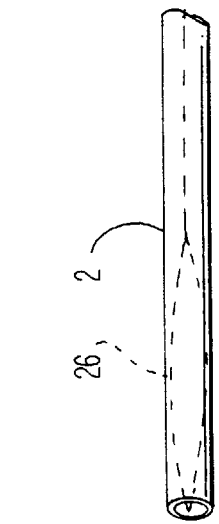
FIG. A PRIOR ART
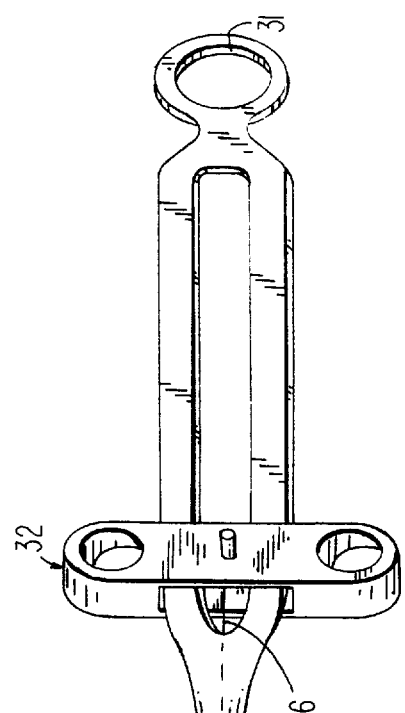
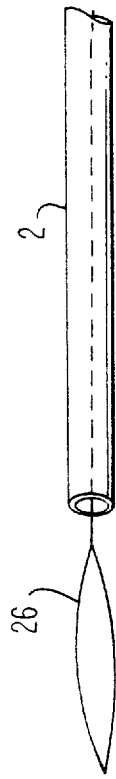
FIG. B PRIOR ART

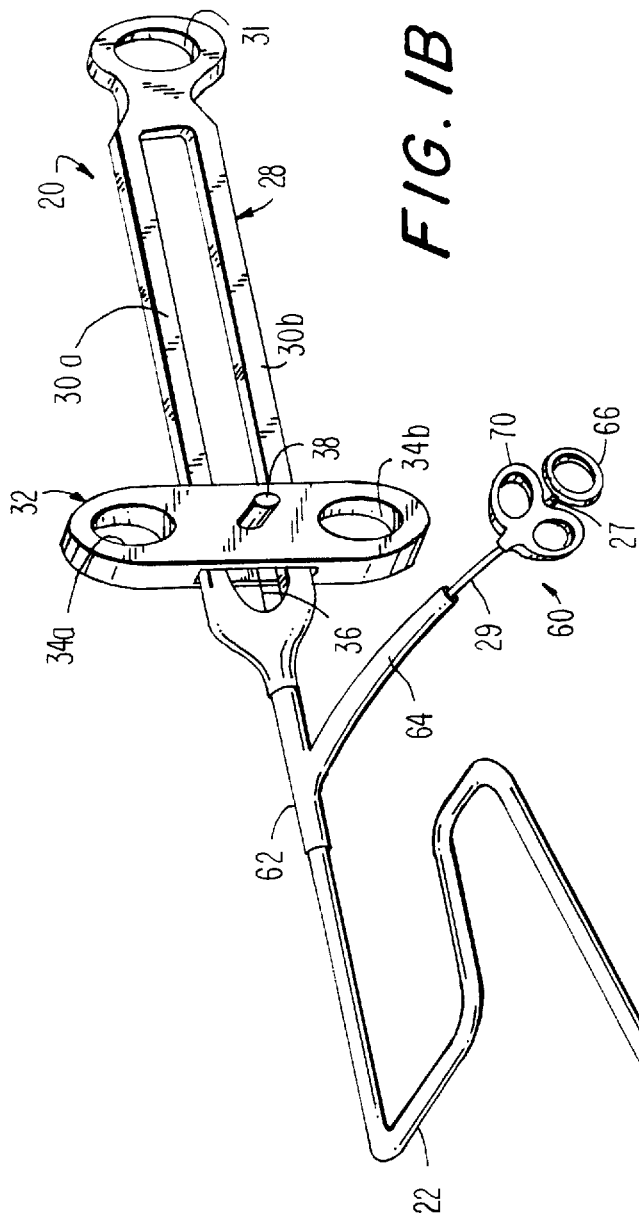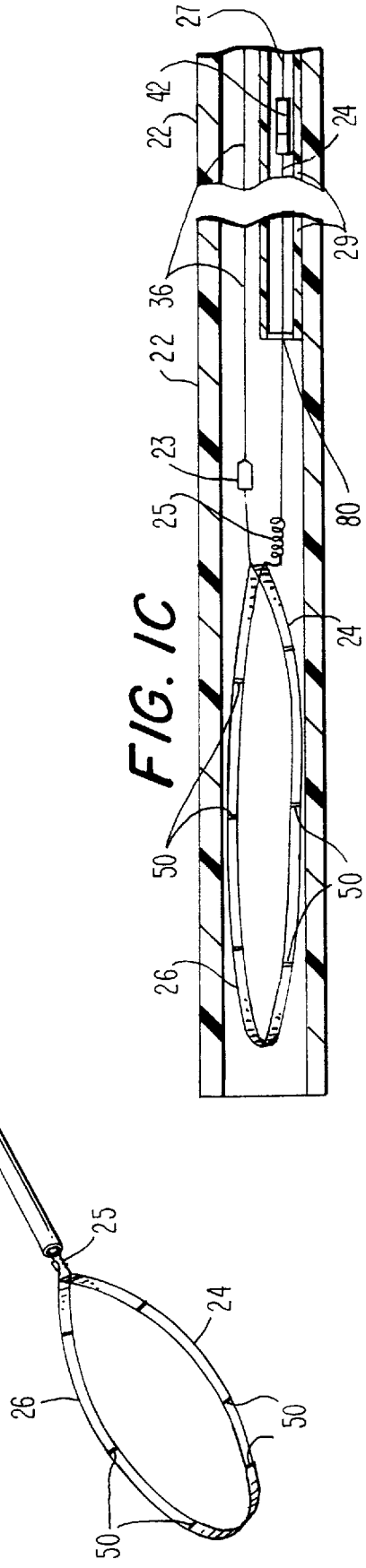

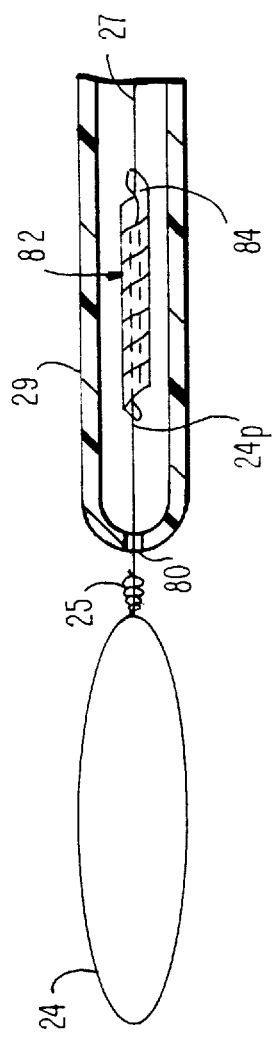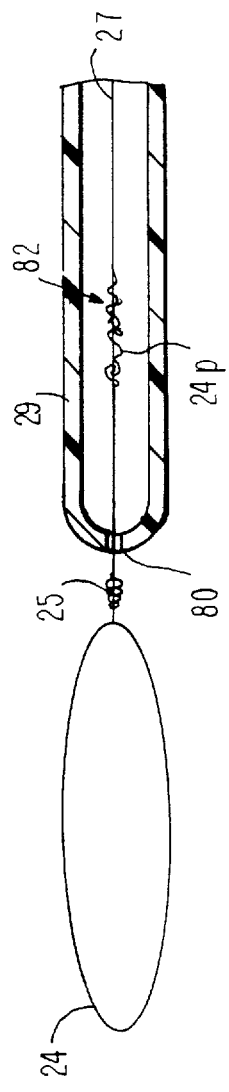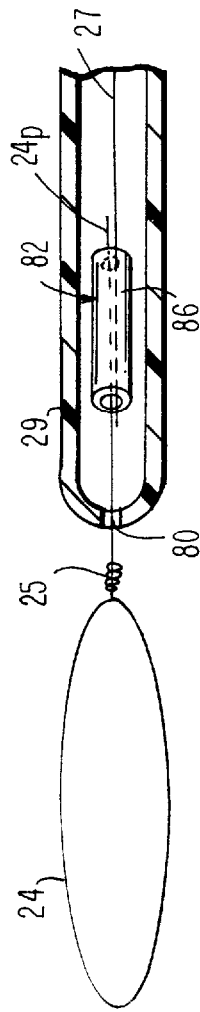

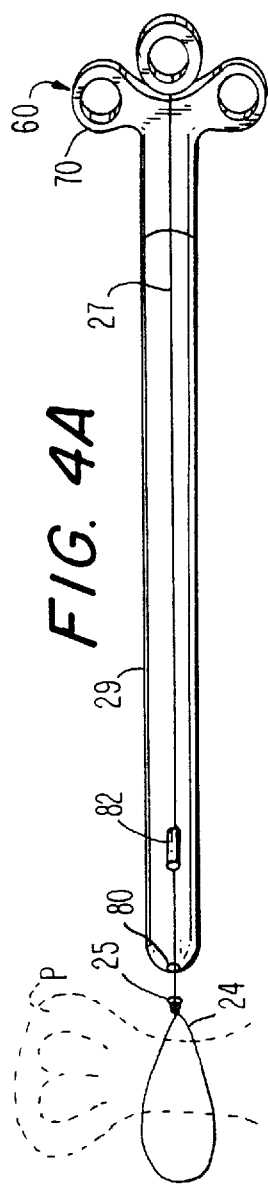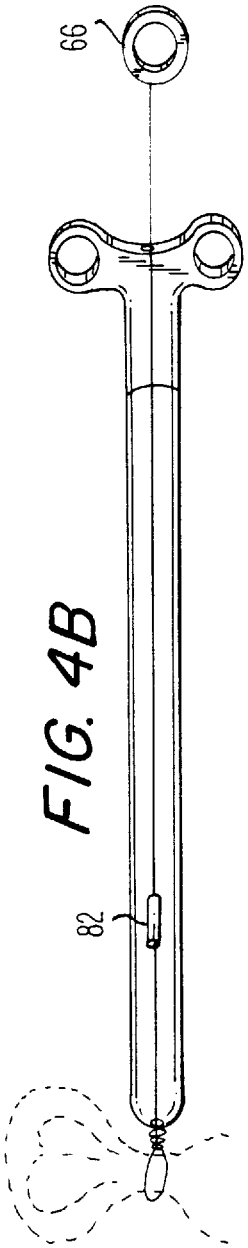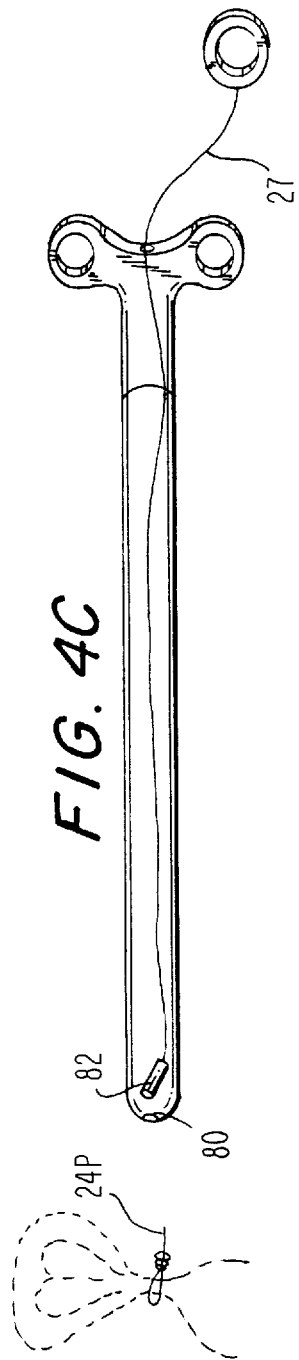

SURGICAL CAUTERIZATION SNARE WITH LIGATING SUTURE

FIELD OF THE INVENTION

The invention relates to endoscopic surgical instruments and methods, and specifically to those for use in procedures employing cauterization snares to resect tissue and organs prior to their removal.

BACKGROUND OF THE INVENTION

Flexible snares introduced by endoscopes are widely used in surgical procedures requiring the removal of selected body tissue or of an organ from inside of a body cavity. The snare, typically a loop or noose formed at the distal end of a flexible metal wire, is moved from the distal end of the endoscope [or laparoscope]* by movement of a handle or plunger attached to its proximal end. The snare can be used in conjunction with cautery in order to cauterize the tissue at the site of the resection and thereby reduce or eliminate bleeding.

However, depending on the size, condition and nature of the tissue or the organ that is to be resected by the snare, complications in the form of excessive bleeding at the site can occur. For example, during a fiberoptic colonoscopy, a polyp is visualized by the endoscopist and the loop of the metal cautery snare is placed around the stalk of the polyp. The proximal end of the snare is attached to an electrical power source. The snare is tightened upon the stalk of the polyp, the cautery is applied and the polyp is transected.

Polyps are pre-malignant lesions which, if left in the colon, become cancerous. There are about 600,000 polypectomies performed each year in the United States alone. Of these, approximately 200,000 procedures involve large polyps. Large polyps are those measuring 2 cm or more in diameter. A polyp of this size is carried by a stalk that has an artery running through it. The artery supplies the polyp with blood, and when the stalk is transected by the snare, there is a danger that this artery will bleed. The larger the polyp, the larger is the blood supplying artery in the stalk and the greater the danger of bleeding.

When such arterial bleeding occurs, the lumen of the colon fills with blood, and it is extremely difficult for the surgeon to see the stalk from which the blood is spouting. If the stalk can be visualized, the endoscopist tries to re-snare the transected stalk, tighten the snare upon it and, if successful, must then hold the snare in this position for 15 minutes hoping for coagulation to occur and for the bleeding to stop. If the bleeding does not stop, or if the stalk cannot be re-snared, the patient has to have immediate surgery, and the segment of colon with the bleeding artery has to be resected.

OBJECTS OF THE INVENTION

An object of the present invention is to provide a safer method for the removal of portions of internal body organs or other selected tissue growths from patients, and especially the removal of large colonic polyps.

A more specific object of the present invention is to provide an improved method for the performance of snare cauterization procedures employing endoscopic and laparoscopic methods and instruments.

Another object of the present invention is to provide a snare cauterization technique wherein the risk of an arterial bleed during a colonoscopic polypectomy is greatly reduced.

Another more particular object of the present invention is to provide a snare cauterization technique wherein potential trauma to the patient and time in surgery are reduced.

A further object of the present invention is to provide a surgical instrument assembly for use in ligating selected portions of body organs or tissue prior to a snare cauterization procedure.

Yet another, more particular object of the present invention is to provide such an instrument assembly which enhances the safety and reliability of snare cauterization procedures for the removal of polyps and other selected body tissues from the internal cavities of patients.

Another particular object of the present invention is to provide such an instrument assembly that is simple to manufacture and therefore inexpensive.

A further particular object of the present invention is to provide such an instrument assembly that is easy to use.

An additional particular object of the present invention is to provide such a surgical instrument assembly which is disposable. A disposable instrument assembly requires no lengthy sterilization procedure and reduces the spread of infectious diseases, such as AIDS.

These and other objects will be apparent from the following description.

SUMMARY OF THE INVENTION

A surgical instrument assembly for use in snare cauterization operations comprises, in accordance with the present invention, a flexible cauterization snare, an electrical conductor operatively connected to the cauterization snare for feeding an electrical current thereto, and a flexible suture member formed into a loop or noose that is releasably connected to the cauterization loop, both the snare and suture members being disposed in a first tubular sheath. The loop in the suture member is formed by a one-way slip knot tied at the distal, or free, end of the suture member. An actuator is operatively connected to the cauterization loop for alternately expanding and contracting the cauterization loop and the auxiliary suture loop. In addition, the suture member is slidably disposed in a second tubular sheath, which in turn is slidably disposed in the first tubular sheath. The second tubular sheath serves to facilitate the release of the suture member from the loop, the positioning of the suture member around the selected body tissue to be ligated, and the tightening of the slip knot to effect the ligature.

The actuator may include a finger ring or knob at a proximal end of the instrument assembly for sliding the cauterization loop and the releasably connected suture member alternately into and out of the distal end of a tubular sheath member.

Preferably, the cauterization loop is made of a metallic material, and the suture member is preferably in the form of a highly flexible, soft multi-filament thread.

Pursuant to another feature of the present invention, the cauterization loop and the suture member are disposed in parallel planes and are contiguous or proximate to one another. The cauterization loop and the suture member can be disposed in essentially the same plane.

According to a specific embodiment of the present invention, the suture member is releasably connected to the cauterization loop by water soluble adhesive or water soluble filaments that dissolve after a brief period of contact with the bodily fluids of the patient at the surgical removal site. The suture member is connected to the metal cauterization loop at a sufficient number of position to insure that it will not be separated prematurely. The proximal end of the suture member, like the cauterization loop, is connected directed, or preferably via elongate tensioning means, to an actuator (such as a push-pull ring or knob) at the proximal end of the instrument assembly. Thus, both the cauterization loop and the suture member are separately controlled by manipulations at the proximal end of the instrument assembly.

As noted above, the assembly further comprises a second tubular sheath member, movably disposed in the first tubular sheath adjacent the electrical conductor, and preferably, elongate tensioning means extending through the second tubular sheath attached to the proximal end of the suture member for tightening the suture member.

Pursuant to another basic conceptualization for the practice of the present invention, a surgical instrument assembly for use in snare cauterization operations comprises a flexible cauterization loop, an electrical conductor operatively connected to the cauterization loop for feeding an electrical current thereto, and a suture member releasably connected thereto. An actuator is operatively connected to the cauterization loop for alternately expanding and contracting the cauterization loop and the releasably connected suture member. As discussed hereinabove with reference to a preferred embodiment of the invention, the proximal end of the suture member is disposed in a second tubular sheath which moves longitudinally inside the first tubular sheath and is operatively connected to a control module at the proximal end thereof. Inside the second sheath and attached to the proximal end of the suture member is an elongate tensioning means, the proximal end of which is operative connected to the control module. The control module comprises actuators in the form of handles, finger and thumb rings and/or knobs operatively connected to the proximal ends of the second tubular sheath and the elongate tensioning means for effecting longitudinal movement of these elements.

A method for removing a selected portion of internal body tissues of a patient comprises, in accordance with the present invention, the steps of: a method of applying a ligature to a selected portion of internal body tissue of a patient prior to removal of the adjacent tissue utilizing a cauterization loop, the method comprising the steps of:

(a) providing a conductive cauterization loop to which a flexible suture member is releasably connected, a slip knot in the distal end of the suture member forming a loop;

(b) at least partially expanding said cauterization loop and connected suture member from a collapsed configuration to an expanded configuration;

(c) passing the expanded suture member and connected loop over the selected body tissue to be removed;

(d) partially closing the cauterization loop and attached suture member around the selected body tissue to be removed;

(e) releasing said suture member from the cauterization loop;

(f) advancing the slip knot on the suture member to securely tighten the suture loop around a base region of the internal body tissue thereby form a ligature;

(g) closing said cauterization loop so that said cauterization loop engages said selected internal body tissue adjacent to the ligature;

(h) completing the cauterization procedure to sever and remove the selected internal body tissue.

The present invention provides an improved method for the removal from patients of selected tissue, such as polyps, and internal body organs, via snare cauterization, which method greatly reduces the risk of internal bleeding at the site of the polypectomy or other surgery.

In a method in accordance with the present invention, ligation to reduce or eliminate bleeding at the site of a snare cauterization procedure is provided. An instrument assembly in accordance with the present invention is simple to use. Accordingly, risk of hemorrhage and surgery are reduced. More specifically, time under anaesthesia with the accompanying side effects is reduced. Concomitantly, the expense of hospitalization is decreased.

BRIEF DESCRIPTION OF THE DRAWINGS

FIGS. A and B are perspective schematic views, partially in phantom, illustrating the elements of a snare cautery device of the prior art.

FIG. 1B is a perspective view of the snare cauterization instrument assembly of FIG. 1A in an extended, open configuration.

FIG. 1C is a schematic longitudinal cross-sectional view of a distal end of the cauterization instrument assembly of FIG. 1A, showing the cauterization loop and suture member in a withdrawn or retracted storage configuration prior to use inside the distal end of a tubular member of the instrument assembly.

FIGS. 3A–3C are schematic longitudinal cross sectional views, showing different specific embodiments of a portion of the snare cauterization instrument assembly for releasing the suture member after completing the ligature.

FIGS. 4A–4C are a series of perspective schematic views illustrating a portion of the surgical instrument assembly of FIGS. 1A–1C in isolation.

DETAILED DESCRIPTION

Figure 1A:
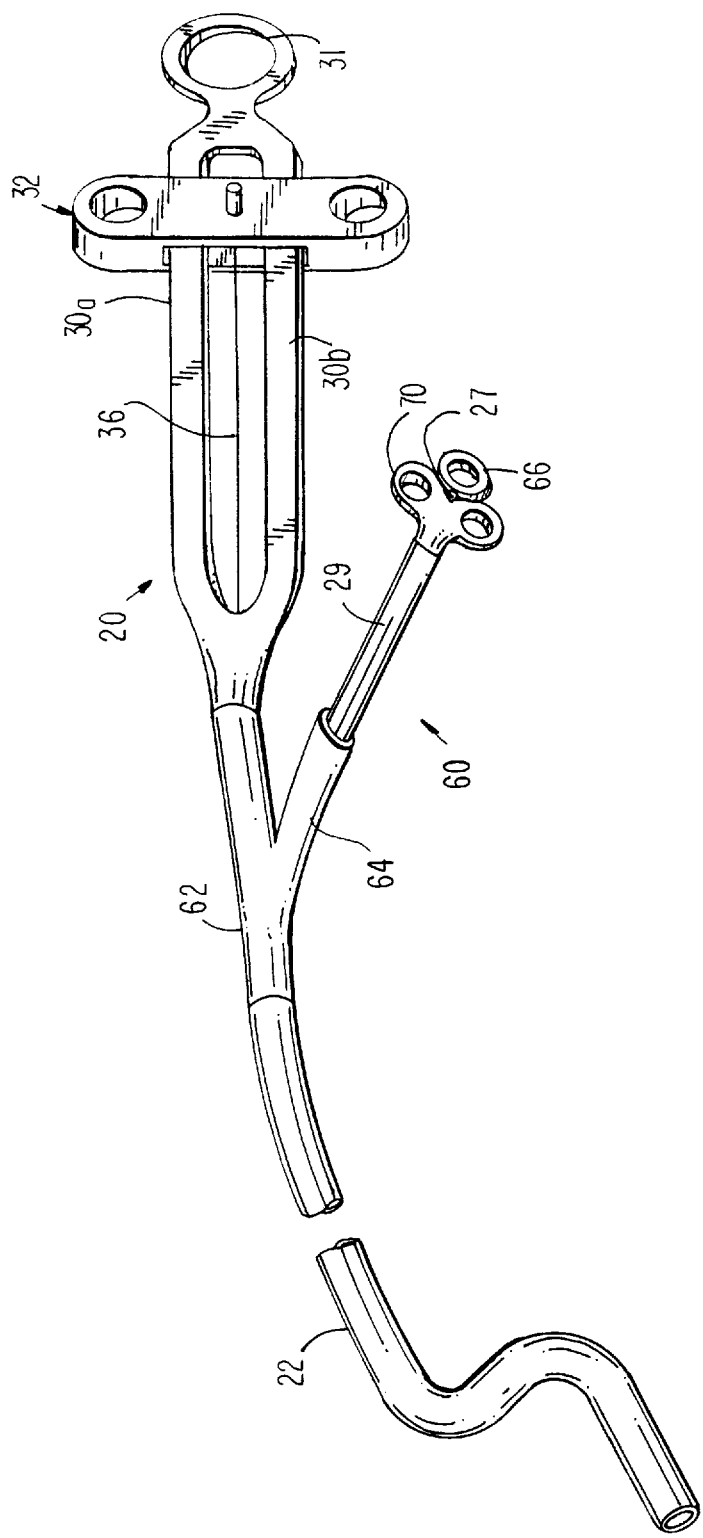
FIG. 1A is a perspective view of one embodiment of a snare cauterization instrument assembly of the invention in a closed or ready configuration, prior to insertion in the biopsy channel of an endoscope.

A device for snare cautery constructed with elements known to the prior art is illustrated in FIGS. A and B, and comprises a hand-held snare actuator module 10, a flexible tubular member 2 connected to a distal end of the control module, and an alternately expandable and closable cauterization loop 26 at the distal tip of the first tubular member 2.

Snare actuator module 10 comprises a body member or frame 28 which includes a pair of parallel rails 30a and 30b to which a slider member 32 is reciprocatably secured. Frame 28 has a thumb hole 31 at a proximal end, whereas slider member 32 has a pair of finger holes 34a and 34b and is fastened to the proximal end of an electrically conductive wire 36 which passes through tubular sheath 2 and is joined to cauterization loop 26. Wire 36 is sufficiently flexible to bend with tubular member 2 during the negotiation thereby of curves or bends in a colon during surgery. The snare cauterization device is maintained in the closed or withdrawn configuration of FIG. A as it is inserted into the biopsy channel of an endoscope. When the endoscope is in position and the tissue to be removed has been visualized, the loop is advanced to the position illustrated in FIG. B.

Slider member 32 is also provided with an electrical connector 38 which is couplable to a source of electrical energy. During a severing step of a cauterization operation, described in detail hereinafter, electrical energy is fed to loop 26 via connector 38 and wire 36.

The snare cauterization instrument assembly of the invention, as illustrated in FIGS. 1A and 1B, comprises a hand-held control module 20, a flexible first tubular sheath member 22 that is connected to a distal end of the control module 20. A flexible suture member 24 formed with a one-way slip knot 25 at its distal end is releasably connected to cauterization loop 26. Electrically conductive wire 36 is joined to cauterization loop 26 by junction member 23 proximate the distal end of first tubular member 22.

As shown in FIGS. 1B and 1C, suture member 24 is releasably joined to loop 26 by a plurality of joining means 50. As will be described in greater detail below, joining means 50 functions to retain the flexible suture member 24 proximate loop 26 for positioning about the tissue to be ligated, and then permits the suture member 24 to be separated from loop 26. The joining means 50 can take the form of filaments or fibers, a film or web, an adhesive or like material that can function to temporarily secure the flexible suture material from which member 24 is formed to the flexible wire forming loop 26. The joining means 50, after release of the suture member from loop 26, must not interfere with the movement of slip knot 25 as it is tightened around the tissue to form a ligature. As an alternative to forming a plurality of individual points of attachment as illustrated in FIG. 1B, where a film or web, or adhesive compound is employed, joining means 50 can be continuous. Joining means 50 can be formed from thermoplastic or heat degradable materials that will melt and/or degrade at the cauterization temperature attained by loop 26 upon application of an electrical current.

As will be appreciated by one of ordinary skill in the art from the relationship of the elements illustrated in FIG. 1C, the inside diameter of first tubular sheath 22 must be sufficient to permit the easy passage of second tubular sheath 29 and electrical wire 36. The inside diameter of second sheath 29 must be sufficient to accommodate the longitudinal movement of suture release means 82, and terminates at its distal end in a tip provided with orifice 80. The diameter of orifice 80 is selected to permit the free passage of the suture member 24, and small enough so that the outer edge of the tip will engage slip knot 25 and will prevent the passage of release means 82 from sheath 29.

Suture actuator module 60 is also joined to the distal end of control module 20, and includes Y-fitting 62 with branch member 64 that communicate with the axial passage in first sheath 22 through which wire 36 passes. Extending from branch member 64 is the proximal end of elongate tensioning means 27 joined to finger ring 66. Also extending from the opening in member 64 is the proximal end of second tubular sheath 29, which terminates in finger ring 70. As will be discussed in more detail below, finger ring 70 can be removably engaged with slider 32 in order to coordinate the advancement of second tubular sheath 29 and conductor wire 36 to facilitate the alignment and positioning of cauterization loop 26 and suture member 24.

Prior to the beginning of a snare cauterization operation, loop 26 is disposed in a contracted state together with releasably connected suture member 24 in the distal end of tubular member 22, as illustrated in FIG. 1C. Concomitantly, slider member 32 is retracted to the proximal end of rails 30a and 30b (towards the right side of frame 28 in FIG. 1A). Tubular member 22 is inserted in a biopsy channel 40 of an endoscope 42, as shown in FIG. 2A, and the endoscope is inserted into a body cavity of a patient, such as a colon C.

Figure 2A:
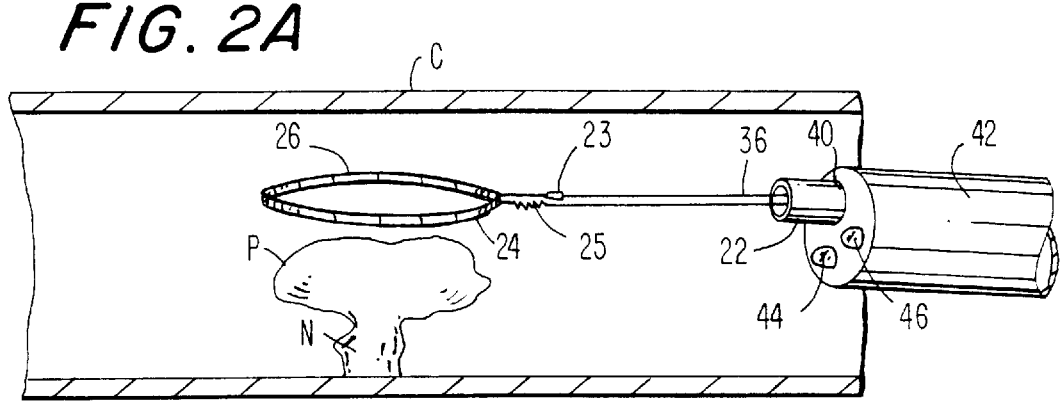
FIG. 2A is a schematic partial cross sectional view of a patient's colon with a polyp, showing the snare cauterization instrument assembly of FIG. 1A inserted in the biopsy channel of an endoscope which is itself inserted into the patient's colon, and further showing the instrument assembly in an initial stage of a snare cauterization procedure.

As illustrated further in FIG. 2A, endoscope 42 is conventionally provided at its distal end with a pair of apertures 44 and 46 for, respectively, delivering light to, and receiving light from a surgical site.

Upon the observation of a polyp P within colon C via the use of endoscope 42, the snare cauterization instrument assembly is shifted in a distal direction so that tubular member 22 protrudes from the distal end of biopsy channel 40. Then, slider member 32 is shifted in a distal direction to eject loop 26 and releasably connected suture member 24 from tubular member 22. Upon ejection, loop 26 and connected suture member 24 expand from a contracted or closed configuration into an at least partially opened configuration, as shown in FIG. 2A.

Figure 2B:
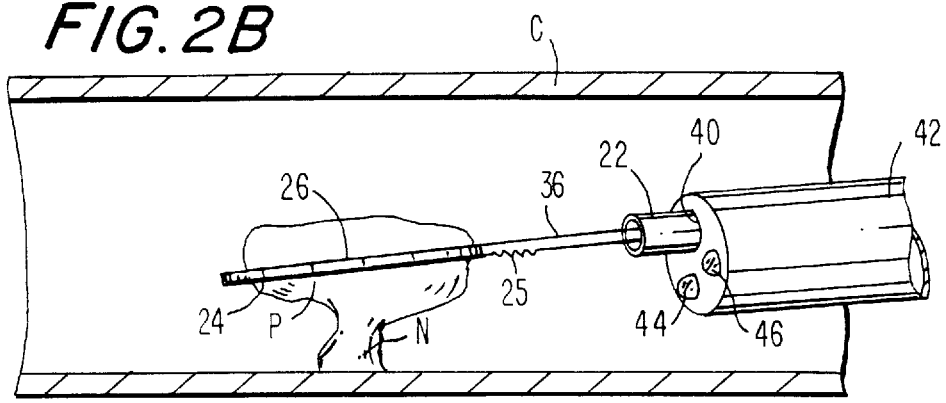
FIG. 2B is a schematic partial cross sectional view similar to FIG. 2A, showing the loop and the connected suture member of the snare cauterization instrument assembly of FIG. 1A being passed around e polyp of FIG. 2A.

FIG. 2B depicts a later stage in the cauterization procedure. The snare cauterization instrument assembly of FIG. 1A is manipulated to pass loop 26 and suture member 24 around polyp P.

Figure 2C:
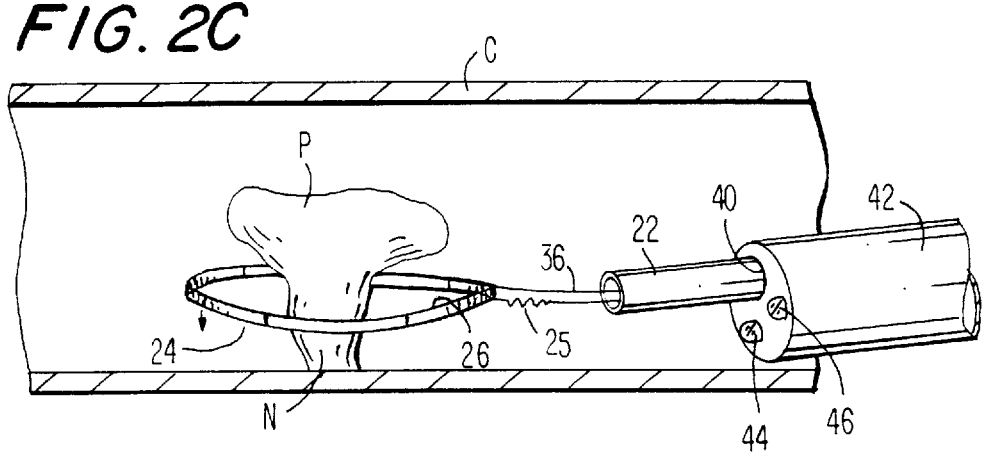
FIG. 2C is a schematic partial cross sectional view similar to FIGS. 2A–2B, showing the loop of the snare cauterization instrument assembly of FIG. 1A completely passed around the polyp of FIG. 2A.
Figure 2D:
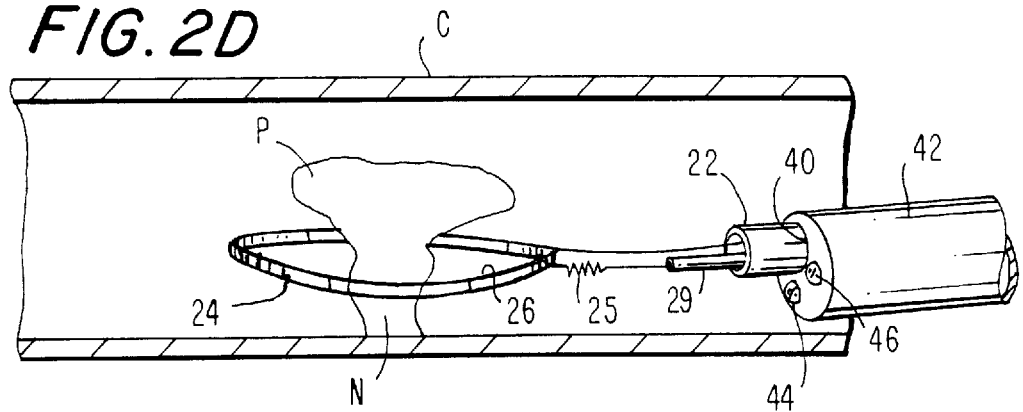
FIG. 2D is a schematic partial cross sectional view similar to FIGS. 2A–2C, showing the suture member of the snare cauterization instrument assembly of FIG. 1A being tightened around a base or neck of the polyp.

As shown in FIG. 2C, the loop 24 and suture member 24 are lowered over the polyp P, at which position bodily fluid will come into contact with the water soluble filaments 50 that join the loop and suture member, dissolving them. In order to assist in separating suture member 24 from loop 26 and to position suture member for the ligation, second tubular sheath 29 is advanced from the distal end of first sheath 22, as shown in FIG. 2D. Cauterization loop 26 is also partially closed around the tissue of polyp P.

Figure 2E:
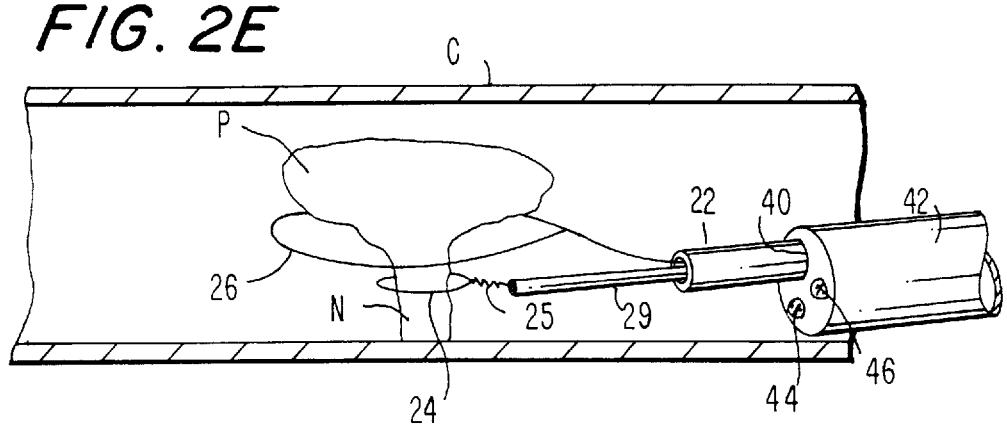
FIG. 2E is a schematic partial cross sectional view similar to FIGS. 2A–2D, showing the completed ligature and the loop of the snare cauterization instrument assembly of FIG. 1A in an electrically energized state for burning through the base or neck of the polyp.

Following its release and separation from loop 26, suture member 24 encircles a base region or neck N of polyp P and the polyp is surrounded by suture member 26, as shown in FIG. 2E.

Figure 2F:
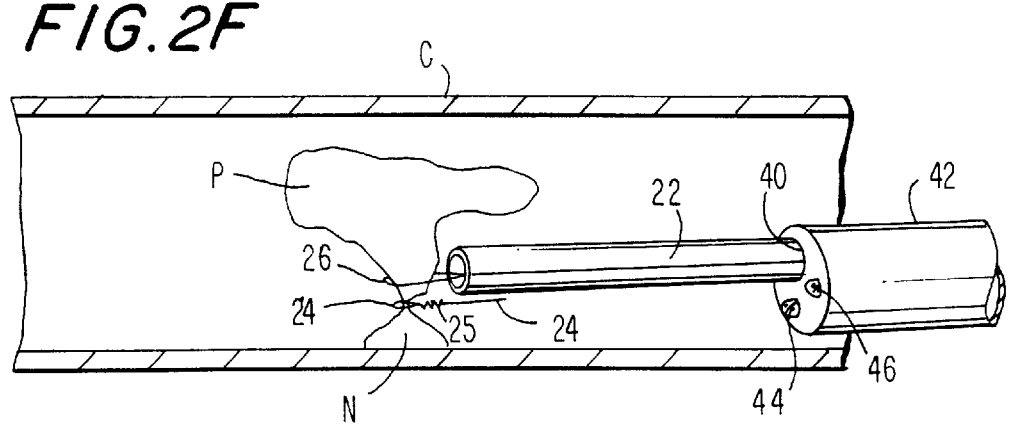
FIG. 2F is a schematic partial cross sectional view similar to FIGS. 2A–2E, showing the polyp severed from the colon wall and release of the proximal end of the suture member prior to removal of the cauterization instrument assembly of FIG. 1A.

Once the suture member is in the desired position at the base section of the polyp P, the distal end of second sheath 29 is further advanced against slip knot 25 by movement of finger ring 70 while simultaneously withdrawing tensioning means 27 by finger ring 66. After the suture member has been tightened about the base or stalk of polyp P and the ligation thereby completed, the cauterization loop is tightened against the adjacent section of the polyp base towards its free end above the suture and current is applied in order to sever the polyp, as shown in FIG. 2F.

As one step in the procedure, the proximal end of the suture member is released from the distal end of the elongated tensioning means 27. The release of the proximal end of suture member 24 from the surgical instrument assembly is effected in conjunction with suture release means 82. As shown in more detail in FIGS. 3A–C, suture release means 82 comprises a temporary joining of the proximal end 24P of suture member 24 with the distal end of the elongate tensioning means 27 so that proximal end 24P can be removed from the instrument assembly after the ligature is formed. FIG. 3A illustrates an embodiment where the ends of suture member 24P and tensioning means 27 are overlapped and tightly wrapped with a band or web 44 of flexible material, such as a polymeric material. One end of web 44 can be bonded to elongated tensioning means 27 and when the suture member is to be separated, tensioning means 27 is rotated to loosen the web 84; thereafter the tensioning means 27 is moved proximally and the free end 24P of suture member 24 passes through orifice 80 in sheath 29.

As schematically illustrated in the embodiment of FIG. 3B, the ends of the suture member 24P and tensioning means 27 are twisted around each other to temporarily join them. In order to insure a sufficiently strong connection during the tightening of the ligature, a water soluble bonding agent can be applied as part of the suture release means 82. After securing the ligature, second tubular sheath 29 is moved proximally and release means 42 passes through orifice 80 and into contact with body fluids at the site to solubilize the bonding agent and release the free end 24P of the suture member.

FIG. 3C illustrates yet another embodiment where suture release means 82 comprises an elastomeric sleeve through which pass the proximal end of suture member 24 and the distal end of elongate tensioning means 27 in an overlapping configuration. The inward radial pressure exerted by elastomeric band 86 is sufficient to maintain the overlapping relation during the tightening of the ligature; after the ligature is formed, additional tension is applied by moving tensioning means 27 proximally to release the proximal end of suture member 24 from band 86. The diameter of the band 86 is larger than orifice 80 to insure that the band is not left at the surgical site, but is retained in second tubular sheath 29. As will be apparent to one skilled in the art, modifications to the structures and methods described above can be undertaken in the construction of alternate suture release means.

Where the two ends are releasable under the application of a tensioning force, the finger ring 66 is withdrawn further while the tip of the second sheath 29 is maintained in position against the tightened skip know 25, as shown, for example, in FIG. 2E. Once sufficient tensioning force has been applied to part the distal end of tensioning means 27 from the suture member at 27P, the second tubular sheath 29 is withdrawn from first tubular sheath 22, and from the instrument assembly.

Where the two ends are joined by a spirally wrapped filament or web, as illustrated in FIG. 3A, the finger ring 66 is turned in a direction opposite to the spiral wrap until the proximal end of the suture 24P can be pulled free. Where the two ends are joined by water soluble binder means, the joined section is placed in contact with the bodily fluids proximate the surgical site to dissolve the binder and the ends are freed by the application of tension to the tensioning means 27.

At that juncture, slider member 32 is pulled back in the proximal direction, whereby wire 36 pulls loop 24 further back into the distal end of tubular member 22, thereby causing loop 24 to tighten about neck N of polyp P, as illustrated in FIG. 2F.

As also indicated in FIG. 2F, electrical current is then caused to pass through wire 36 and loop 24. Generally, electric current from loop 24 is conducted through neck N of polyp P, thereby generating in the polyp tissues heat sufficiently great to sever and cauterize neck N. Upon the severing of polyp P at neck N, slider member 32 is pulled farther in the proximal direction, thereby pulling loop 24 further into the distal end of tubular member 22 to essentially close the loop. In a final step, the entire snare cauterization instrument assembly including, in particular, tubular member 22, is shifted in the proximal direction relative to endoscope 42.

In order to further illustrate the method and apparatus of the invention, reference is made to FIGS. 4A–C where there is shown in isolation the suture member 24, second tubular sheath 29 and actuator module 60 and related elements. As shown in FIG. 4A, following its separation from cauterization loop 26 by the release of joining means 50, the loop of suture member 24 is placed over the polyp and positioned towards the base of the stalk. Finger ring 70 attached to sheath 29 is advanced distally until the tip surrounding orifice 80 of sheath 29 contacts the slip knot 25. Tension is maintained on elongate tensioning means 27 via finger ring 66 and finger ring 70 is further advanced distally to tighten slip knot 25 around the stalk of polyp P to form the ligature, as is shown in FIG. 4B. While the tip surrounding orifice 80 is maintained in contact with slip knot 25, proximal end 24P of suture member 24 is separated from suture release means 82, for example, as shown in connection with FIGS. 3A–3C above. Thereafter, as shown in FIG. 4C, sheath 29 containing release means 82 and tensioning means 27 are withdrawn from the surgical site prior to the cauterization step.

Figure 5A:
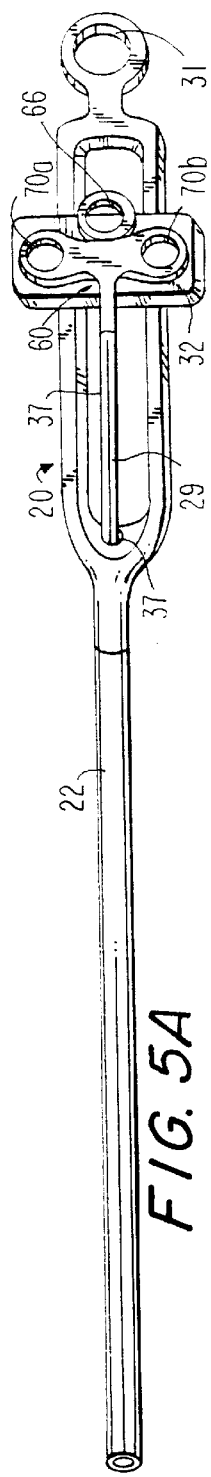
FIGS. 5A–5E are a series of perspective schematic views of another embodiment of the surgical instrument assembly illustrating its method of use.
Figure 5B:
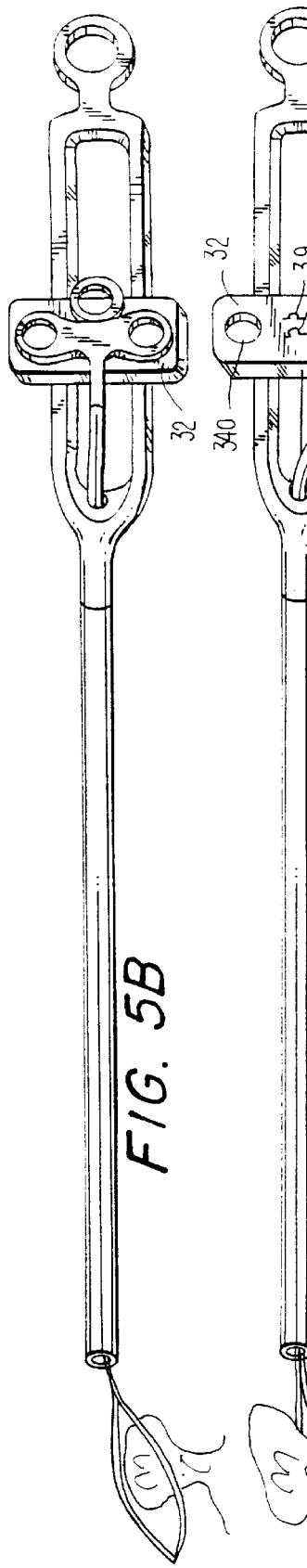

In the further preferred embodiments illustrated in FIGS. 5A–5E, second tubular sheath 29 passes through orifice 37 in control module 20 co-axially with electrically conductive wire 37. As can be seen in FIGS. 5A and 5B, finger rings 70 and 66 which comprise actuator module 60 are temporarily joined to the slider member 32 so that openings 70a and 34a and openings 70b and 34b are aligned when the cauterization loop 26 and suture member 24 are in the starting or retracted position in the first sheath 22. The actuator module and slider member are releasably joined by mating means 39, such as snap or press fit projections and corresponding recesses on the respective parts, rotationally interlocking surfaces (not shown), hook and loop fasteners (sold under the trademark VELCRO®) secured to the surface to be joined (not shown), and the like. It will be appreciated that mating means 39 are desirable to position the parts in aligned relation so that the surgeon's fingers can be passed through the openings in finger rings 70 and 34 to simultaneously advance the wire 36 and tensioning means 27.

Figure 5C:
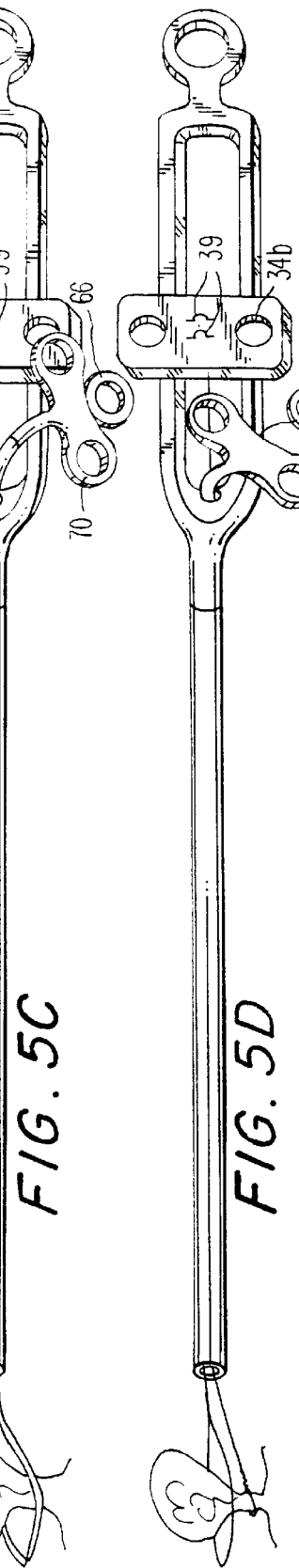
Figure 5D:
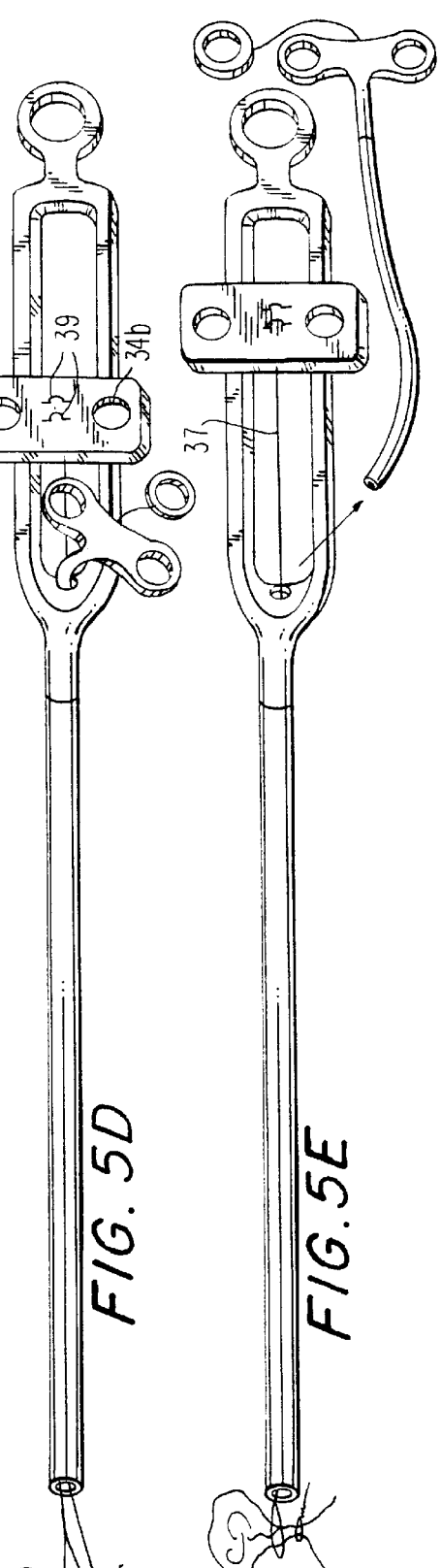
Figure 5E:
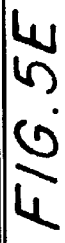

As will be understood by reference to the sequence illustrated by FIGS. 2A–2F, and the corresponding description, movement of the slider member 32 in the distal direction, i.e., from FIG. 5A to FIG. 5B, advances loop 26 from the interior of first sheath 22, thereby permitting it to open with releasably attached suture member 24. As illustrated in FIG. 5C, actuator module 60 is then separated from slider member 32. Finger ring 66 is held in position with a tensioning force, and simultaneously assembly 70 is distally advanced to move the tip of second sheath 29 into contact with slip knot 25. FIG. 5D illustrates the relative position of the above elements when the ligature has been formed by the fully tightened suture member 24. Following release of the proximal end 24D of the suture member, the second tubular sheath 29 and related actuator module 60 are fully withdrawn from the first tubular sheath through orifice 80 in the distal end of control module 20.

In a like manner, suture actuator module 60 can be temporarily mated with slider member 32 in the embodiments illustrated in FIGS. 1 and 2 by appropriate orientation of branch 64 of Y-fitting 62 (not shown). The second tubular sheath 29 should be of sufficient flexibility and resiliency to provide a smooth channel for tensioning means 27.

Although not specifically shown in FIGS. 5A–5E, it will be understood that the necessary cautery connections are made to electrically conductive wire 36 either prior to, or following completion of the ligature. In the practice of this invention, the cauterization step is performed after the ligature is completed.

Every polyp ligated and severed by a snare cauterization instrument as described and illustrated herein should produce little, if any, bleeding. Thus, the time for the procedure will be reduced to a minimum. Trauma to the patient from potential complications due to excessive bleeding is likewise reduced, as are hospitalization expenses.

A cauterization instrument assembly as described herein is of relatively simple construction, is inexpensive to produce and is preferably disposable.

Although the invention has been described in terms of particular embodiments and applications, one of ordinary skill in the art, in light of this teaching, can generate additional embodiments and modifications without departing from the spirit of, or exceeding the scope of the claimed invention. Accordingly, it is to be understood that the drawings and descriptions herein are proffered by way of example to facilitate comprehension of the invention and should not be construed to limit the scope thereof.

We claim:

1. A surgical instrument assembly for use in snare cauterization procedures comprising:
   a first tubular sheath member;
   loop means for forming a cauterization loop which is alternatively expandable and contractible in essentially a single plane, a proximal end of said loop means configured to operatively mate with an electrically conductive wire passing longitudinally through said first tubular sheath to electrical supply means for supplying a current to said loop means;
   a second tubular sheath member slidably disposed in the first tubular sheath member;
   a flexible suture member releasably connected to the loop means, a distal end of the suture member forming a one-way slip knot and a proximal end of the suture member disposed in the distal end the second tubular sheath;
   an actuator module associated with the proximal end of the second tubular sheath for advancing said second tubular sheath distally with respect to the distal end of the first tubular sheath;
   elongate tensioning means releasably joined to the proximal end of the suture member and disposed in the second tubular sheath, a proximal end of the tensioning means joined to the actuator module where the second tubular sheath and tensioning means cooperate to advance said slip knot on the suture member.

2. The instrument assembly of claim 1 where the suture member is connected to the loop means at a plurality of spaced locations.

3. The instrument assembly of claim 1 where the suture member is a multi-filament thread.

4. The instrument assembly of claim 1 where the suture member is formed of bioabsorbable material.

5. The instrument assembly of claim 1 where the suture member is releasably connected to the loop means by filaments.

6. The instrument assembly of claim 1 where the suture member is releasably connected to the loop means by a film.

7. The instrument assembly of claim 1 where the suture member is releasably connected to the loop means by thermoplastic means.

8. The instrument assembly of claim 7 where the thermoplastic means is a plurality of filaments.

9. The instrument assembly of claim 1 where the suture member is releasably connected to the loop means by water soluble means.

10. The instrument assembly of claim 9 water soluble means is a solidified liquid adhesive.

11. The instrument assembly of claim 1 where the elongate tensioning means is the same material as the suture member.

12. The instrument assembly of claim 1 where the elongate tensioning means is a flexible wire.

13. The instrument assembly of claim 1 where the elongate tensioning means is releasably joined to the suture member by water soluble bonding means.

14. The instrument assembly of claim 13 where the water soluble bonding means is water soluble adhesive.

15. The instrument assembly of claim 13 where the water soluble bonding means is a water soluble filament.

16. The instrument assembly of claim 13 where the water soluble bonding means is a water soluble web.

17. The instrument assembly of claim 1 where the elongate tensioning means is releasably joined to the suture member by spiral wound web means.

18. The instrument assembly of claim 17 where the spiral wound web means is attached to the elongate tensioning means.

19. The instrument assembly of claim 1 where the proximal end of the suture member is wrapped around the distal end of the elongate tensioning means.

20. The instrument assembly of claim 1 where the elongate tensioning means is releasably joined to the suture member by a slip knot.

21. The instrument assembly of claim 1 where the distal end of the second tubular sheath terminates in an orifice of a diameter smaller than the inside diameter of the proximal end of said second sheath.

22. The instrument assembly of claim 21 where the diameter of the orifice in the distal end of the second tubular sheath is smaller than the one-way slip knot in the suture member.

23. The instrument assembly of claim 1 where the actuator module comprises a first manually operable means connected to the proximal end of the second tubular sheath for advancing and retracting said second sheath relative to said first tubular sheath and a second manually operable means connected to the proximal end of the elongate tensioning means.

24. The instrument assembly of claim 23 where the second manually operated means is rotatable about the longitudinal axis of the elongate tensioning means.

25. The instrument assembly of claim 23 where the first manually operable means comprises at least one finger ring and an axial passage for slidably receiving said elongate tensioning means.

26. The instrument assembly of claim 25 where the second manually operable means comprises at least one finger ring.

27. The instrument assembly of claim 1 further comprising a snare control module operably connected to the proximal end of said electrically conductive wire and said control module being joined to the proximal end of the first tubular sheath.

28. The instrument assembly of claim 27 where the control module further comprises at least one finger ring operably attached to said conductive wire to effect the longitudinal movement of the cauterization loop relative to the first tubular sheath.

29. The instrument assembly of claim 27 further comprising mating means for releasably joining the actuator module and the control module for simultaneous longitudinal movement of the elongate tensioning means and the conductive wire.

* * * * *